US011335342B2

(12) United States Patent
Nagar et al.

(10) Patent No.: US 11,335,342 B2
(45) Date of Patent: May 17, 2022

(54) VOICE ASSISTANCE SYSTEM

(71) Applicant: International Business Machines Corporation, Armonk, NY (US)

(72) Inventors: Raghuveer Prasad Nagar, Kota (IN); Sarbajit K. Rakshit, Kolkata (IN); Jagadesh Ramaswamy Hulugundi, Bangalore (IN); Reji Jose, Bangalore (IN)

(73) Assignee: International Business Machines Corporation, Armonk, NY (US)

( * ) Notice: Subject to any disclaimer, the term of this patent is extended or adjusted under 35 U.S.C. 154(b) by 273 days.

(21) Appl. No.: 16/797,604

(22) Filed: Feb. 21, 2020

(65) Prior Publication Data

US 2021/0264908 A1 Aug. 26, 2021

(51) Int. Cl.
| | | |
|---|---|---|
| *G10L 15/00* | (2013.01) | |
| *G10L 15/22* | (2006.01) | |
| *G06F 3/16* | (2006.01) | |
| *G02C 7/04* | (2006.01) | |
| *A61B 3/113* | (2006.01) | |
| *A61B 5/16* | (2006.01) | |
| *G02B 27/00* | (2006.01) | |
| *G02B 27/01* | (2006.01) | |

(52) U.S. Cl.
CPC ............ *G10L 15/22* (2013.01); *A61B 3/113* (2013.01); *A61B 5/165* (2013.01); *G02B 27/0093* (2013.01); *G02B 27/0101* (2013.01); *G02C 7/04* (2013.01); *G06F 3/167* (2013.01); *G10L 2015/223* (2013.01)

(58) Field of Classification Search
CPC ................................ G10L 15/22; G06F 3/015
See application file for complete search history.

(56) References Cited

U.S. PATENT DOCUMENTS

| | | | |
|---|---|---|---|
| 9,442,310 B2 | 9/2016 | Biederman | |
| 10,366,691 B2 | 7/2019 | Rochford | |
| 2007/0066916 A1* | 3/2007 | Lemos | A61B 5/165 |
| | | | 600/558 |
| 2007/0182595 A1* | 8/2007 | Ghasabian | G06F 1/1632 |
| | | | 341/22 |
| 2013/0212501 A1* | 8/2013 | Anderson | G06F 3/011 |
| | | | 715/764 |
| 2016/0299354 A1 | 10/2016 | Shtukater | |
| 2017/0023793 A1 | 1/2017 | Shtukater | |

(Continued)

FOREIGN PATENT DOCUMENTS

WO 2015127062 A1 8/2015

OTHER PUBLICATIONS

Elgan, "Why a smart contact lens is the ultimate wearable," Computerworld, May 2016, 6 pages.

*Primary Examiner* — Daniel Abebe
(74) *Attorney, Agent, or Firm* — VanLeeuwen & VanLeeuwen; James L. Olsen (57) ABSTRACT

An approach is provided in which the approach captures a voice command spoken by a user along with a set of data generated from a smart contact lens worn by the user. The approach matches the set of data to a command augmentation indicator that identifies an augmentation to the voice command. The approach aggregates the command augmentation indicator with the voice command into an aggregated command and executes the aggregated command accordingly.

17 Claims, 8 Drawing Sheets

(56) References Cited

U.S. PATENT DOCUMENTS

| | | |
|---|---|---|
| 2017/0160813 A1 | 6/2017 | Divakaran |
| 2017/0221484 A1* | 8/2017 | Poltorak ................ G06V 40/28 |
| 2017/0262051 A1* | 9/2017 | Tall .................... G06F 3/04842 |
| 2017/0270636 A1* | 9/2017 | Shtukater ............... G02C 11/10 |
| 2018/0136492 A1 | 5/2018 | An |
| 2019/0126484 A1 | 5/2019 | Benaim |
| 2019/0236416 A1 | 8/2019 | Wang |
| 2021/0081952 A1* | 3/2021 | Rakshit ................... G06F 3/013 |
| 2021/0166685 A1* | 6/2021 | Myoga ................ G06V 40/197 |
| 2021/0191506 A1* | 6/2021 | Wang .................. G06N 3/0454 |

\* cited by examiner

| Data Translation Table 360 ||
|---|---|
| Oculesics Data | Command Augmentation Indicator |
| tears, fluctuating eyelids | happy |
| tears, closed eyelids | sad |
| wink | return opposite answer |
| double blink | wake up |
| wide open eye lids | surprise/anxiety |
| narrowing eye lids | uncomfortable/angry/stress |
| | |

VOICE ASSISTANCE SYSTEM

BACKGROUND

Today's voice assistance systems are centralized home or office automation devices that perform tasks or services for an individual based on commands or questions. The voice assistance systems provide a wide variety of services, such as providing weather information, providing facts from an online database, setting alarms, generating to-do lists, playing music from streaming services, playing radio stations, reading audiobooks, and etcetera.

A voice assistance system typically waits for a "wakeup" command prior to responding to a user request, which is typically a specific phrase spoken by the user. Once woken, the voice assistance system interprets human speech and responds via synthesized voices. The user asks the voice assistance system questions, control home automation devices, control media playback, and manage other basic tasks using verbal commands.

BRIEF SUMMARY

According to one embodiment of the present disclosure, an approach is provided in which the approach captures a voice command spoken by a user along with a set of data generated from a smart contact lens worn by the user. The approach matches the set of data to a command augmentation indicator that identifies an augmentation to the voice command. The approach aggregates the command augmentation indicator with the voice command into an aggregated command and executes the aggregated command accordingly.

The foregoing is a summary and thus contains, by necessity, simplifications, generalizations, and omissions of detail; consequently, those skilled in the art will appreciate that the summary is illustrative only and is not intended to be in any way limiting. Other aspects, inventive features, and advantages of the present disclosure, as defined solely by the claims, will become apparent in the non-limiting detailed description set forth below.

BRIEF DESCRIPTION OF THE SEVERAL VIEWS OF THE DRAWINGS

The present disclosure may be better understood, and its numerous objects, features, and advantages made apparent to those skilled in the art by referencing the accompanying drawings, wherein.

DETAILED DESCRIPTION

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions. The following detailed description will generally follow the summary of the disclosure, as set forth above, further explaining and expanding the definitions of the various aspects and embodiments of the disclosure as necessary.

Figure 1:
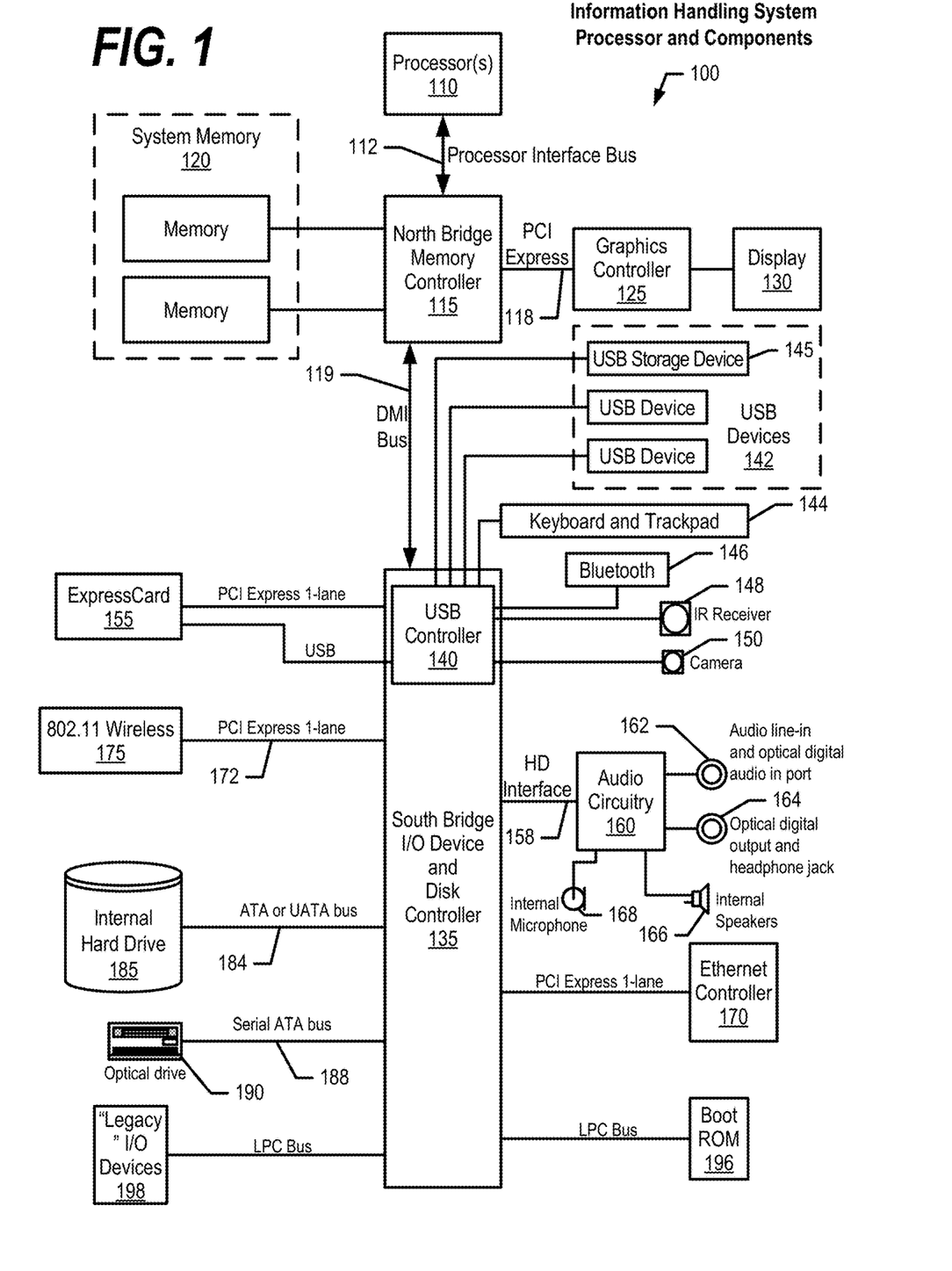
FIG. 1 is a block diagram of a data processing system in which the methods described herein can be implemented.

FIG. 1 illustrates information handling system 100, which is a simplified example of a computer system capable of performing the computing operations described herein. Information handling system 100 includes one or more processors 110 coupled to processor interface bus 112. Processor interface bus 112 connects processors 110 to Northbridge 115, which is also known as the Memory Controller Hub (MCH). Northbridge 115 connects to system memory 120 and provides a means for processor(s) 110 to access the system memory. Graphics controller 125 also connects to Northbridge 115. In one embodiment, Peripheral Component Interconnect (PCI) Express bus 118 connects Northbridge 115 to graphics controller 125. Graphics controller 125 connects to display device 130, such as a computer monitor.

Northbridge 115 and Southbridge 135 connect to each other using bus 119. In some embodiments, the bus is a Direct Media Interface (DMI) bus that transfers data at high speeds in each direction between Northbridge 115 and Southbridge 135. In some embodiments, a PCI bus connects the Northbridge and the Southbridge. Southbridge 135, also known as the Input/Output (I/O) Controller Hub (ICH) is a chip that generally implements capabilities that operate at slower speeds than the capabilities provided by the Northbridge. Southbridge 135 typically provides various busses used to connect various components. These busses include, for example, PCI and PCI Express busses, an ISA bus, a System Management Bus (SMBus or SMB), and/or a Low Pin Count (LPC) bus. The LPC bus often connects lowbandwidth devices, such as boot ROM 196 and "legacy" I/O devices (using a "super I/O" chip). The "legacy" I/O devices (198) can include, for example, serial and parallel ports, keyboard, mouse, and/or a floppy disk controller. Other components often included in Southbridge 135 include a Direct Memory Access (DMA) controller, a Programmable Interrupt Controller (PIC), and a storage device controller, which connects Southbridge 135 to nonvolatile storage device 185, such as a hard disk drive, using bus 184.

ExpressCard 155 is a slot that connects hot-pluggable devices to the information handling system. ExpressCard 155 supports both PCI Express and Universal Serial Bus (USB) connectivity as it connects to Southbridge 135 using both the USB and the PCI Express bus. Southbridge 135 includes USB Controller 140 that provides USB connectivity to devices that connect to the USB. These devices include webcam (camera) 150, infrared (IR) receiver 148, keyboard and trackpad 144, and Bluetooth device 146, which provides for wireless personal area networks (PANs). USB Controller 140 also provides USB connectivity to other miscellaneous USB connected devices 142, such as a mouse, removable nonvolatile storage device 145, modems, network cards, Integrated Services Digital Network (ISDN) connectors, fax, printers, USB hubs, and many other types of USB connected devices. While removable nonvolatile storage device 145 is shown as a USB-connected device, removable nonvolatile storage device 145 could be connected using a different interface, such as a Firewire interface, etcetera.

Wireless Local Area Network (LAN) device 175 connects to Southbridge 135 via the PCI or PCI Express bus 172. LAN device 175 typically implements one of the Institute of Electrical and Electronic Engineers (IEEE) 802.11 standards of over-the-air modulation techniques that all use the same protocol to wirelessly communicate between information handling system 100 and another computer system or device. Optical storage device 190 connects to Southbridge 135 using Serial Analog Telephone Adapter (ATA) (SATA) bus 188. Serial ATA adapters and devices communicate over a high-speed serial link. The Serial ATA bus also connects Southbridge 135 to other forms of storage devices, such as hard disk drives. Audio circuitry 160, such as a sound card, connects to Southbridge 135 via bus 158. Audio circuitry 160 also provides functionality associated with audio hardware such as audio line-in and optical digital audio in port 162, optical digital output and headphone jack 164, internal speakers 166, and internal microphone 168. Ethernet controller 170 connects to Southbridge 135 using a bus, such as the PCI or PCI Express bus. Ethernet controller 170 connects information handling system 100 to a computer network, such as a Local Area Network (LAN), the Internet, and other public and private computer networks.

While FIG. 1 shows one information handling system, an information handling system may take many forms. For example, an information handling system may take the form of a desktop, server, portable, laptop, notebook, or other form factor computer or data processing system. In addition, an information handling system may take other form factors such as a personal digital assistant (PDA), a gaming device, Automated Teller Machine (ATM), a portable telephone device, a communication device or other devices that include a processor and memory.

Figure 2:
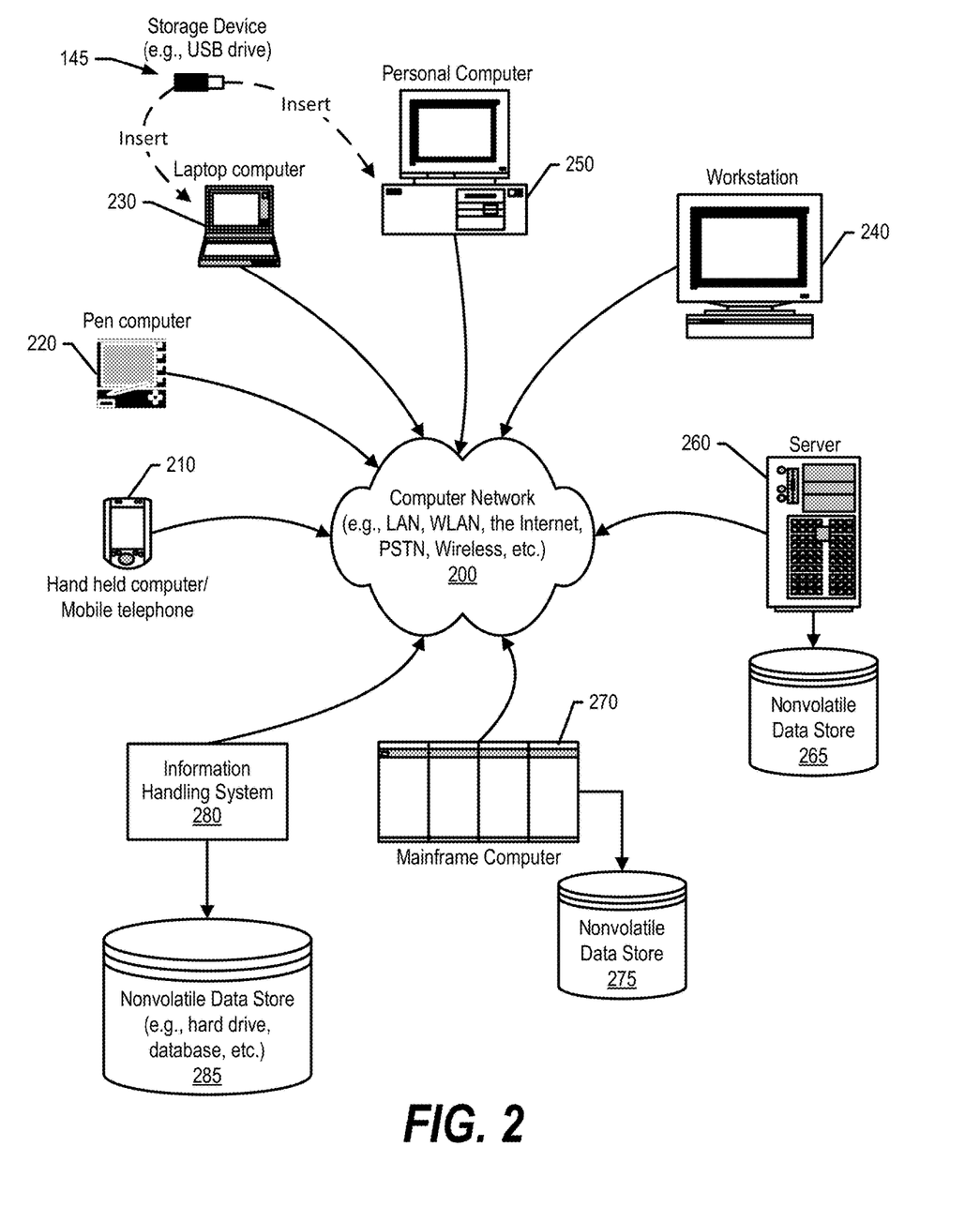
FIG. 2 provides an extension of the information handling system environment shown in FIG. 1 to illustrate that the methods described herein can be performed on a wide variety of information handling systems which operate in a networked environment.

FIG. 2 provides an extension of the information handling system environment shown in FIG. 1 to illustrate that the methods described herein can be performed on a wide variety of information handling systems that operate in a networked environment. Types of information handling systems range from small handheld devices, such as handheld computer/mobile telephone 210 to large mainframe systems, such as mainframe computer 270. Examples of handheld computer 210 include personal digital assistants (PDAs), personal entertainment devices, such as Moving Picture Experts Group Layer-3 Audio (MP3) players, portable televisions, and compact disc players. Other examples of information handling systems include pen, or tablet, computer 220, laptop, or notebook, computer 230, workstation 240, personal computer system 250, and server 260. Other types of information handling systems that are not individually shown in FIG. 2 are represented by information handling system 280. As shown, the various information handling systems can be networked together using computer network 200. Types of computer network that can be used to interconnect the various information handling systems include Local Area Networks (LANs), Wireless Local Area Networks (WLANs), the Internet, the Public Switched Telephone Network (PSTN), other wireless networks, and any other network topology that can be used to interconnect the information handling systems. Many of the information handling systems include nonvolatile data stores, such as hard drives and/or nonvolatile memory. The embodiment of the information handling system shown in FIG. 2 includes separate nonvolatile data stores (more specifically, server 260 utilizes nonvolatile data store 265, mainframe computer 270 utilizes nonvolatile data store 275, and information handling system 280 utilizes nonvolatile data store 285). The nonvolatile data store can be a component that is external to the various information handling systems or can be internal to one of the information handling systems. In addition, removable nonvolatile storage device 145 can be shared among two or more information handling systems using various techniques, such as connecting the removable nonvolatile storage device 145 to a USB port or other connector of the information handling systems.

As discussed above, voice assistance systems provide a variety of services based on a user's voice command. A challenge found, however, is that today's voice assistance systems require a verbal wakeup command and do not account for nonverbal information of a user, such as the user's emotional state or nonverbal facial cues. FIGS. 3 through 8 depict an approach that can be executed on an information handling system that receives a user's voice command and aggregates a set of data received from a smart contact lens into an aggregated command that the voice assistance system executes.

In one embodiment, the set of data is oculesics data. Oculesics data is data that corresponds to the user's eye behavior including eye lid position/movement, eye pupil dilation/gaze/position/movement, eye lid position/movement, and eye tears. The approach matches the oculesics data with a predefined command augmentation indicator that indicates an emotional state (happy, sad, etc.) or a runtime command (wakeup, pause, resume, etc.). The approach then aggregates the voice command with the command augmentation indicator to generate an aggregated command and process the aggregated command.

In another embodiment, the smart contact lens captures the user's eye-based behavior (e.g. eye winking) and the voice assistance system delivers a suitable reply. For example, when the user submits a voice command to book a movie ticket while winking, the voice assistance system knows that the user does not want to book the movie ticket. As such, the voice assistance system responds with "movie ticket is not available" so the user can tell their children that the user tried to buy tickets but none were available.

In another embodiment, the approach uses historical learning to classify oculesics data, such as to classify types of tears. For example, a user's tears may correspond to the user laughing, crying, being happy, a problem with eyes etc. In another embodiment, while submitting a voice command, the user can also submit a wakeup command with an eye-based gesture (e.g., one blink).

Figure 3:
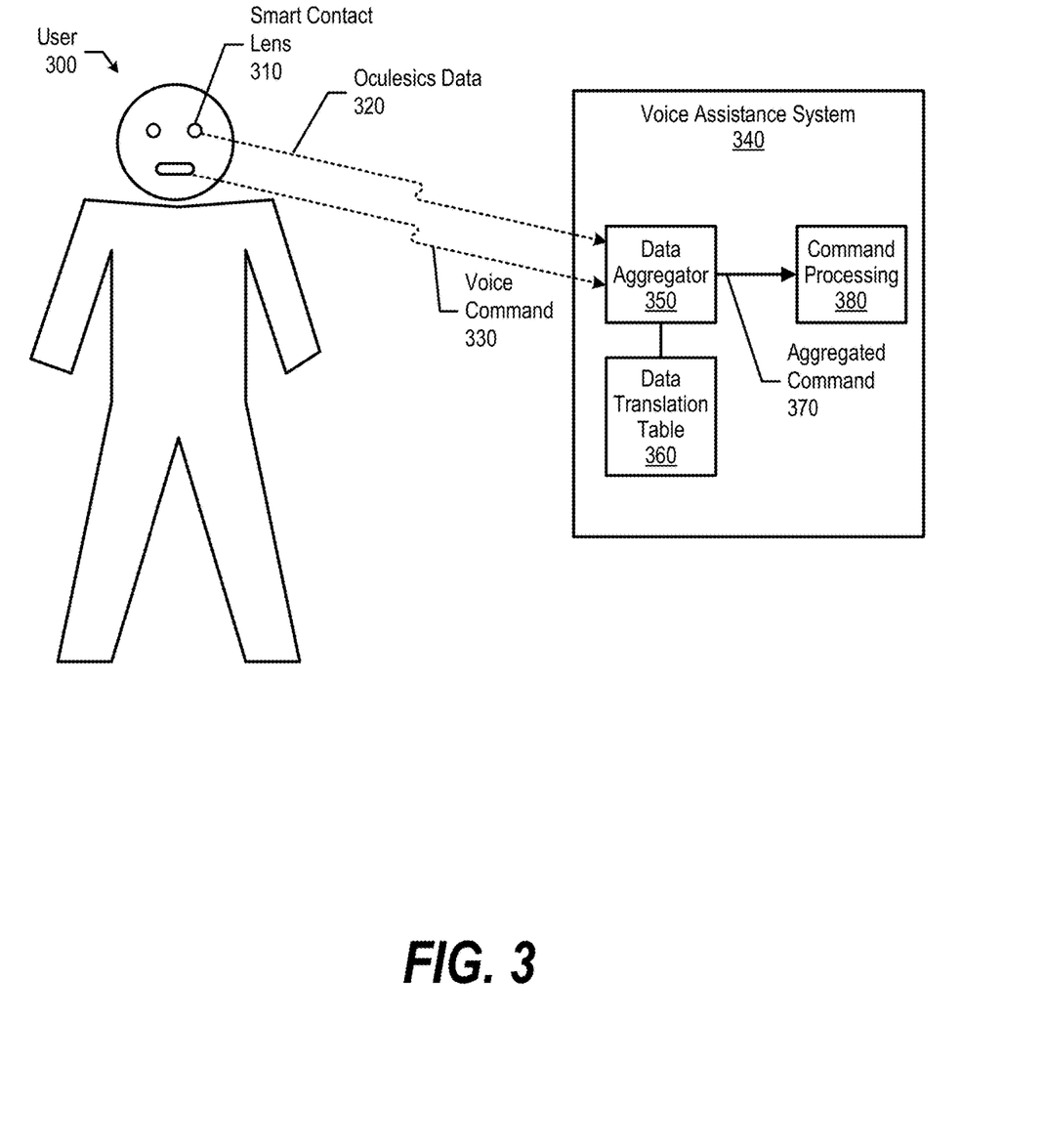
FIG. 3 is an exemplary diagram depicting a voice assistance system aggregating a voice command with oculesics data and processing the aggregated command accordingly.

FIG. 3 is an exemplary diagram depicting a voice assistance system aggregating a voice command with oculesics data and processing the aggregated command accordingly. User 300 wears one or more smart contact lenses 310, which are contact lenses that include sensors and a transmitter (see FIG. 5 and corresponding text for further details). The sensors capture oculesics data (eye behavior) from user 300's eye (blink, tears, eyelids wide open, squinting, etc.) and send oculesics data 320 to voice assistance system 340.

Voice assistance system 340 includes data aggregator 350 that captures oculesics data 320 sent from smart contact lens 310 as well as voice command 330 spoken by user 300. Voice assistance system 340 also includes a preconfigured data translation table 360 that matches oculesics data 320 to a command augmentation indicator. Command augmentation indicators as discussed herein are preconfigured identifiers that identify an emotional state (happy, sad, etc.) or a runtime command (wakeup, play, stop, pause, etc.) (See FIG. 6 and corresponding text for further details).

Data aggregator 350 identifies the command augmentation indicator that matches oculesics data 320 and aggregates the command augmentation indicator with voice command 330 into aggregated command 350. Voice assistance system 340 then processes aggregated command accordingly via command processing 380. In one embodiment, user 300 utilizes a mobile device to perform the data aggregation steps and sends aggregated command 370 to voice assistance system 340 (see FIG. 4 and corresponding text for further details).

In one embodiment, voice assistance system 340 recursively learns user 300's likes/dislikes from user 300's eye behavior. For example, user 300 wishes to follow a live soccer match with much interest, curiousness, and excitement. User 300 asks a question to voice assistance system 340 about today's chance of Team A winning a soccer match. Smart contact lens 310 identifies user 300 through user 300's retina (iris scan) and sends identity data via oculesics data 320 to voice assistance system 340. Voice assistance system 340 authorizes user 300 and starts responding to user 300 about today's soccer match predictions. Smart contact lens 310 captures user 300's cheerfulness by hearing that Team A has a higher probability of winning (e.g., eyes wide open). Voice assistance system 340 now understands that user 300 is interested in following Team A's soccer matches.

Figure 4:
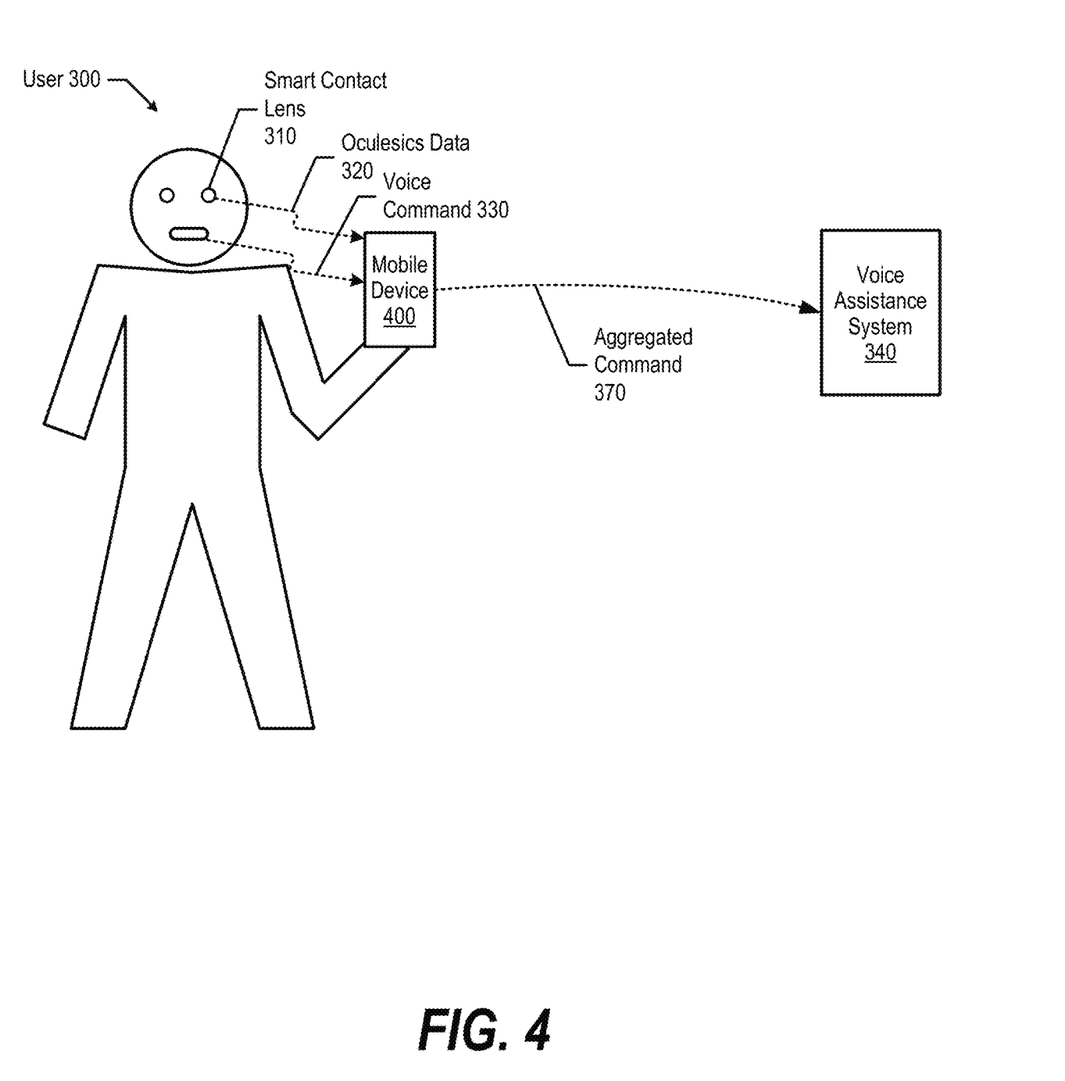
FIG. 4 is an exemplary diagram depicting a mobile device aggregating a voice command with oculesics data and sending the aggregated command to a voice assistance system for processing.

FIG. 4 is an exemplary diagram depicting a mobile device aggregating a voice command with oculesics data and sending the aggregated command to a voice assistance system for processing. FIG. 4 is similar to FIG. 3 with the exception that mobile device 400 includes data aggregator 350 and data translation table 360.

The embodiment shown in FIG. 4 allows user 300 to be positioned further away from voice assistance system 340. Mobile device 400 aggregates voice command 330 with a command augmentation indicator corresponding to oculesics data 320 and sends aggregated command 370 to voice assistance system 340, such as over a cellular or computer network. For example, user 300 may be driving home and very nervous to arrive home alone. Smart contact lens 310 detects user 300's eyes wide open with tears and sends the information via oculesics data 320 to mobile device 400. Mobile device 400 receives voice command 330 to turn the lights on at home and mobile device 400 generates aggregated command 370 accordingly that identifies user 300's nervousness. Mobile device 400 sends aggregated command 370 via cellular network to voice assistance system 340. Voice assistance system 340 understands user 300's emotional state and turns all the lights on inside and outside the house to their highest brightness.

Figure 5:
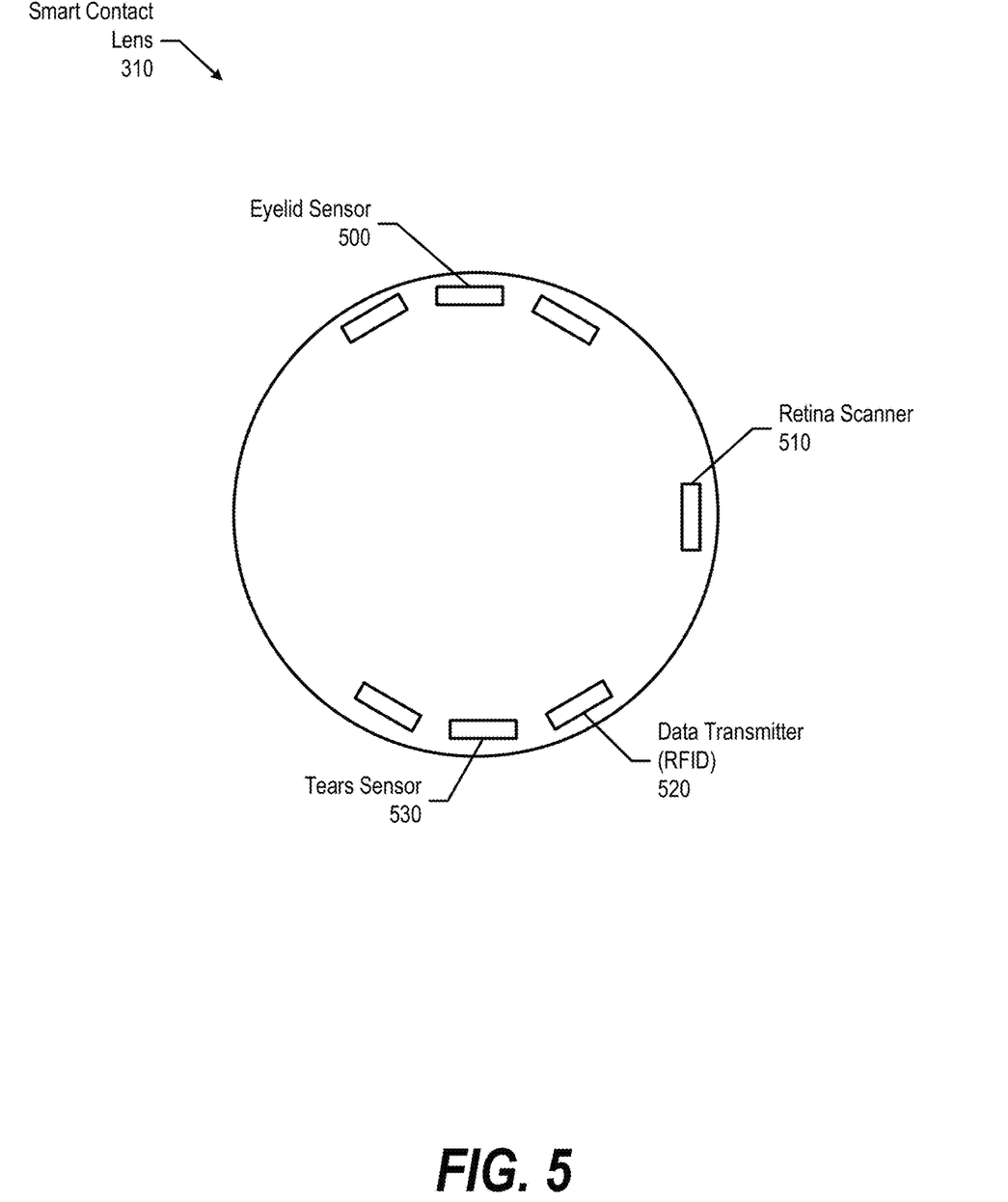
FIG. 5 is an exemplary diagram depicting a smart contact lens that includes multiple sensors and a transmitter.

FIG. 5 is an exemplary diagram depicting a smart contact lens that includes multiple sensors and a transmitter. FIG. 5 shows an embodiment of smart contact lens 310 that includes eyelid sensor 500, retina scanner 510, tears sensor 530, and data transmitter 520.

Eyelid sensor 500 senses user 300's eyelid behavior, such as blinking, closed eye, wide open eye, etc. Retina scanner 510 scans user 300's retina to authorize user 300. Tears sensor 530 detects moisture in user 300's eyes. And, data transmitter 520, which may be an RFID tag, sends oculesics data 320 collected from sensors 500, 510, and 530 to voice assistance system 340 or mobile device 400.

In one embodiment, smart contact lens 310 tracks the way in which user 300 reacts to the tears. For example, if the tears are irritating the eye and user 300 is rubbing the eye, then smart contact lens 310 captures the tears as being a problem with the eye. In another example, if the tears are due to user 300 laughing or crying, voice assistance system 340 analyzes the tone and determines user 300's emotional state.

Figure 6:
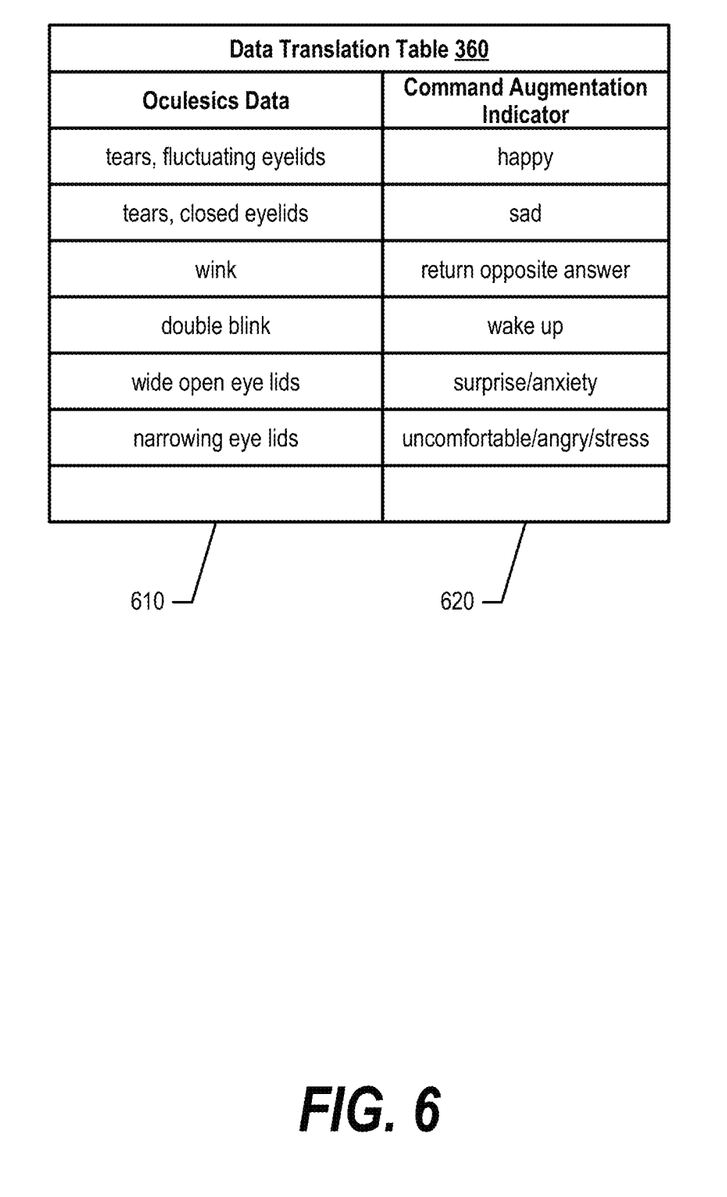
FIG. 6 is an exemplary diagram depicting a data translation table that includes entries containing oculesics data and corresponding command augmentation indicators.

FIG. 6 is an exemplary diagram depicting a data translation table that includes entries containing oculesics data and corresponding command augmentation indicators. User 300 configures data translation table 360 by providing oculesics data and a corresponding command augmentation indicator (see FIG. 7 and corresponding text for further details). Information stored in data translation table 360 may take other forms such as a database, data structure, etc.

Data translation table 360 includes columns 610 and 620. Column 610 includes oculesics data characteristics corresponding to data captured from smart contact lens 310. Column 620 includes command augmentation indicator entries provided by user 300. In one embodiment, voice assistance system 340 provides user 300 with a user interface that allows user 300 to select command augmentation indicators to match oculesics data 320.

Figure 7:
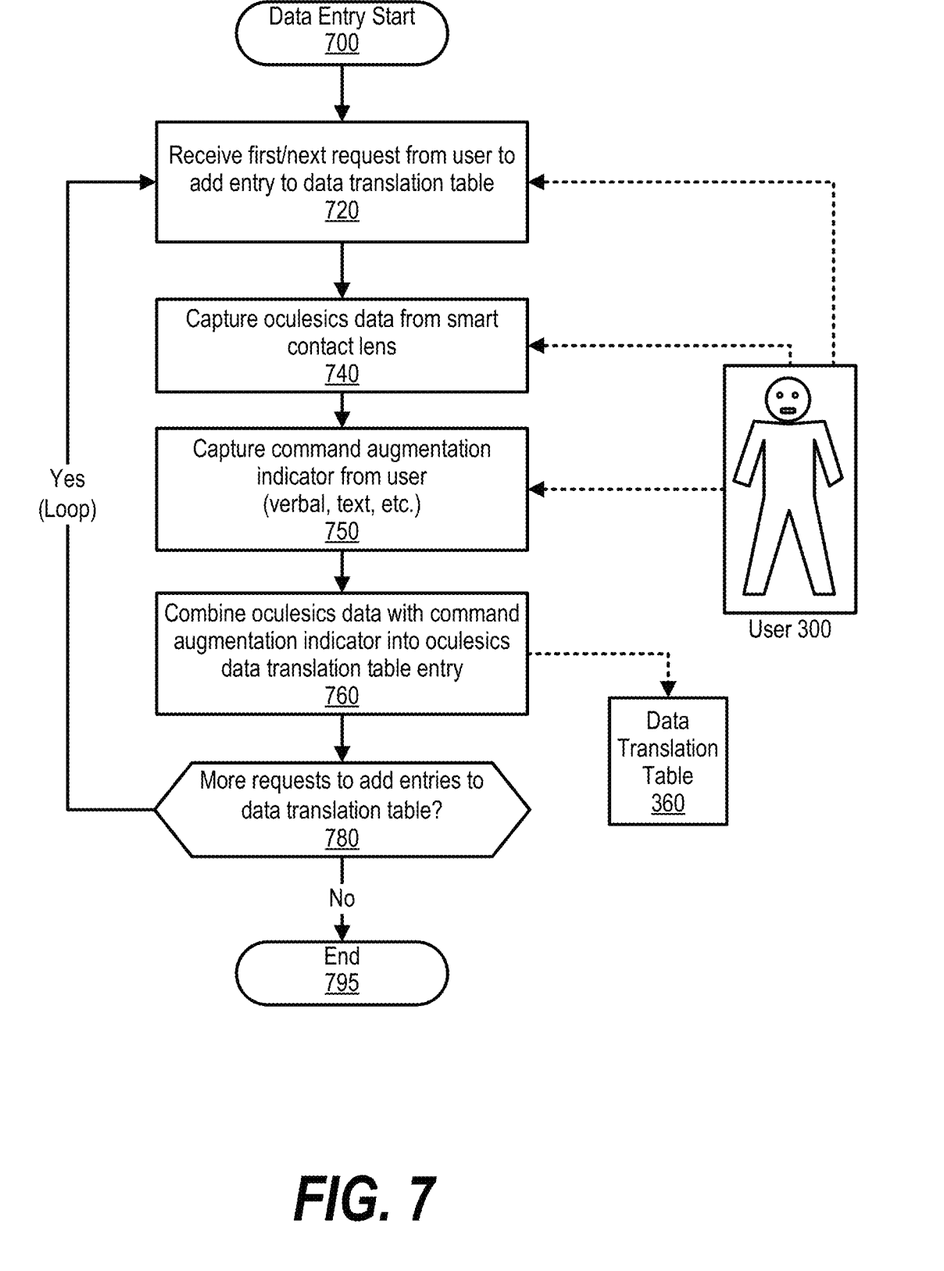
FIG. 7 is an exemplary flowchart depicting steps taken to add oculesics data translation entries to a translation table.

FIG. 7 is an exemplary flowchart depicting steps taken to add oculesics data translation entries to a translation table. FIG. 7 processing commences at 700 whereupon, at step 720, the process receives a request from user 300 to add an entry to data translation table 410. At step 740, the process captures oculesics data 320 from smart contact lens 310 via user 300. For example, the oculesics data may correspond to a widening of user 300's eyelid.

At step 750, the process captures a command augmentation indicator from user 300, such as by user 300 speaking the command augmentation indicator or by user 300 entering the command augmentation indicator on user 300's mobile device 400. At step 760, the process combines the oculesics data with the command augmentation indicator into an oculesics data translation table entry and stores the entry in data translation table 360 (see FIGS. 6, 8, and corresponding text for further details).

The process determines as to whether user 300 wishes to add more entries to data translation table 360 (decision 780). If user 300 wishes to add more entries to data translation table 360, then decision 780 branches to the 'yes' branch which loops back to receive oculesics data and command augmentation indicators from user 300 and add more entries into data translation table 360. This looping continues until user 300 wishes to terminate entry addition steps, at which point decision 780 branches to the 'no' branch exiting the loop. FIG. 7 processing thereafter ends at 795.

Figure 8:
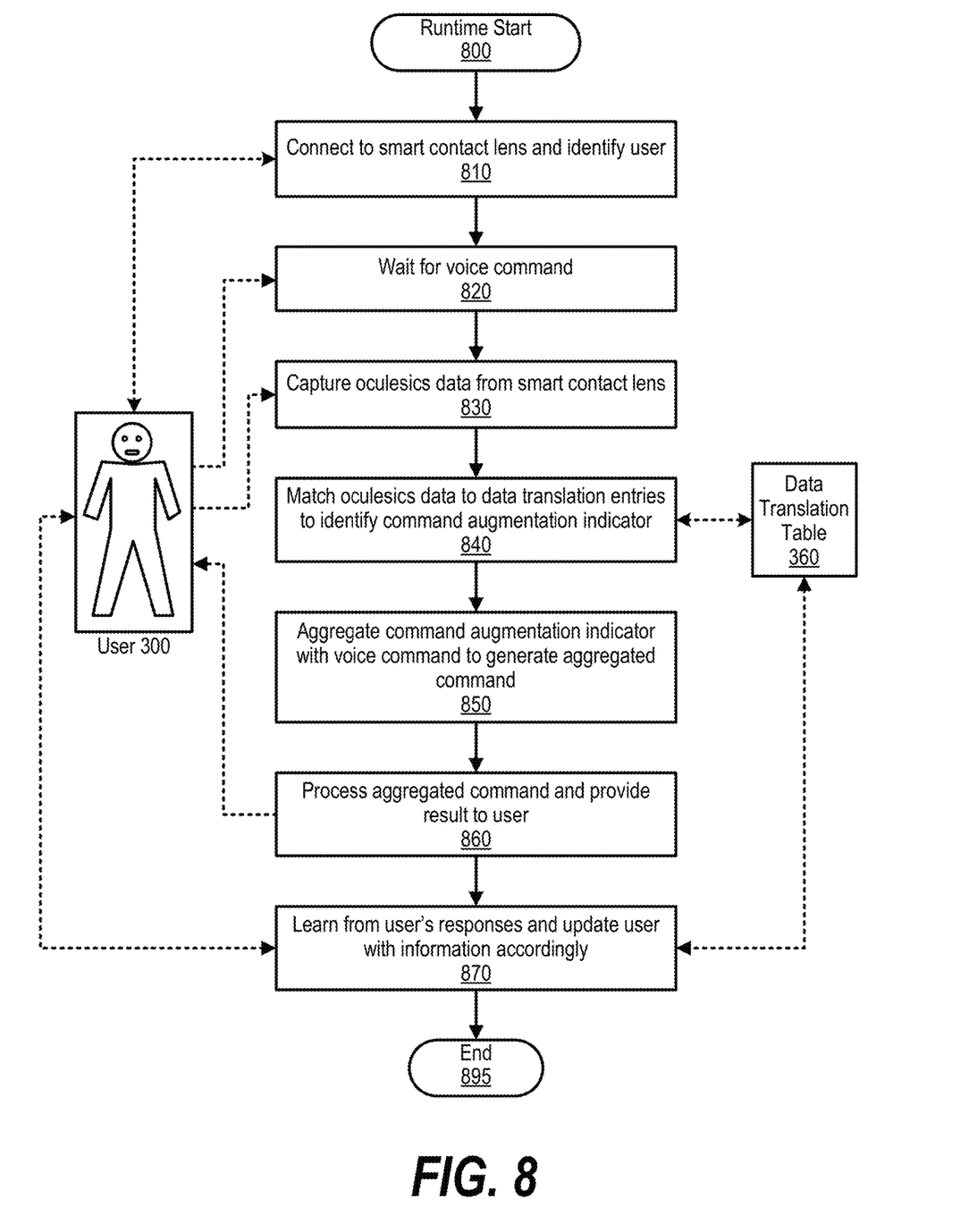
FIG. 8 is an exemplary flowchart showing steps taken to augment a user's voice command based on oculesics data captured from a smart contact lens.

FIG. 8 is an exemplary flowchart showing steps taken to augment a user's voice command with oculesics information captured from a smart contact lens. FIG. 8 processing commences at 800 whereupon, at step 810, the process connects to smart contact lens 310 and identifies user 300. In one embodiment, the oculesics data includes retina scan data that the process utilizes to identify and authorize user 300.

At step 820, the process waits for a voice command from user 300. When the process detects a voice command, the process, at step 830, captures oculesics data from smart contact lens 310. At step 840, the process matches the oculesics data to data translation entries in data translation table 410 to identify a corresponding command augmentation indicator (see FIG. 6 and corresponding text for further details).

At step 850, the process aggregates the command augmentation indicator with the voice command to generate an aggregated command. For example, user 300 may express surprise with his/her eyes wide open upon an unexpected but happy-to-receive visitor at the user 300's house. Based on historical learning, the process determines the past set of patterns of user 300's commands in similar situations where user 300 says "Welcome, delighted to see you." The process aggregates user 300's current command from oculesics data in the context of the situation, applies past learning experiences, and aggregates both of them to generate a "Welcome message" for the visitor who is at user 300's house.

At step 860, the process processes the aggregated command (e.g., accesses the Internet for weather information, sports information, streaming audio, etc.) and provides the result to user 300. At step 870, the process learns from user 300's responses (happy, sad, etc.), adjusts data translation table 360 if required (e.g., modifying existing entries or adding entries), and updates user 300 with information accordingly. For example, voice assistance system 340 determines how often user 300 would like to be informed about a soccer match progress based on user 300's emotional response. Continuing with the example from FIG. 3 above, voice assistance system 340 informs user 300 about the score of Team A's game and smart contact lens 310 captures user 300's excitement and emotions, such as user 300's eyes closed for long time in a soft-pressed manner after hearing the latest score. Smart contact lens 310 sends the information via oculesics data 320 to voice assistance system 340. At half time, voice assistance system 340 updates user 300 about the latest predictions, reviews of experts, winning chances, player's performance, and how the information will impact the second half of the match. Smart contact lens 310 detects the dull emotion captured in user 300's eyes (hard-pressed closing the eyes) and sends the information via oculesics data 320 to voice assistance system 340. Twenty minutes into the second half, voice assistance system 340 updates user 300 of the score and detects the tear drops in user 300's eyes. As such, since voice assistance system 340 understands the context of events and situation, voice assistance system 340 stops updating user 300 of the score until Team A plays better. FIG. 8 processing thereafter ends at 895.

While particular embodiments of the present disclosure have been shown and described, it will be obvious to those skilled in the art that, based upon the teachings herein, that changes and modifications may be made without departing from this disclosure and its broader aspects. Therefore, the appended claims are to encompass within their scope all such changes and modifications as are within the true spirit and scope of this disclosure. Furthermore, it is to be understood that the disclosure is solely defined by the appended claims. It will be understood by those with skill in the art that if a specific number of an introduced claim element is intended, such intent will be explicitly recited in the claim, and in the absence of such recitation no such limitation is present. For non-limiting example, as an aid to understanding, the following appended claims contain usage of the introductory phrases "at least one" and "one or more" to introduce claim elements. However, the use of such phrases should not be construed to imply that the introduction of a claim element by the indefinite articles "a" or "an" limits any particular claim containing such introduced claim element to disclosures containing only one such element, even when the same claim includes the introductory phrases "one or more" or "at least one" and indefinite articles such as "a" or "an"; the same holds true for the use in the claims of definite articles.

The invention claimed is:

1. A method implemented by an information handling system that includes a memory and a processor, the method comprising:
    capturing a voice command and a set of oculesics data corresponding to a user, wherein the voice command is spoken by the user and the set of oculesics data is generated from a smart contact lens worn by the user;
    matching the set of oculesics data to a command augmentation indicator, wherein the command augmentation indicator indicates an augmentation to the voice command;
    aggregating the command augmentation indicator with the voice command into an aggregated command;
    executing the aggregated command by a voice assistance system;
    receiving a different set of oculesics data from the smart contact lens;
    determining that the different set of oculesics data corresponds to a runtime control operation; and
    executing the runtime control operation by the voice assistance system.

2. The method of claim 1 wherein the set of oculesics data is selected from a group consisting of eye lid data, eye tear data, and eye pupil data.

3. The method of claim 2 further comprising:
    capturing the different set of oculesics data in response to executing the aggregated command;
    determining an emotional state of the user based on the different set of oculesics data; and
    adjusting a future aggregated command based on the determined emotional state.

4. The method of claim 2 further comprising:
    receiving the set of oculesics data and the voice command at a mobile device utilized by the user;
    performing, by the mobile device, the matching of the set of oculesics data to the command augmentation indicator and the aggregating of the command augmentation indicator with the voice command; and
    transmitting the aggregated command from the mobile device to the voice assistance system.

5. The method of claim 2 further comprising:
    waking up the voice assistance system based on the command augmentation indicator.

6. The method of claim 1 further comprising:
inhibiting the executing of the aggregated command in response to determining that the command augmentation indicator indicates not to execute the voice command.

7. The method of claim 1 further comprising:
prior to the capturing of the set of oculesics data:
  capturing a set of oculesics training data from the smart contact lens;
  receiving the command augmentation indicator from the user;
  creating a table entry that combines the set of oculesics training data with the command augmentation indicator; and
  storing the table entry in a data translation table; and
accessing the data translation table during the matching of the set of oculesics data to the command augmentation indicator.

8. The method of claim 1 wherein the smart contact lens comprises a tears sensor, an eyelid sensor, and a data transmitter.

9. An information handling system comprising:
one or more processors;
a memory coupled to at least one of the processors;
a set of computer program instructions stored in the memory and executed by at least one of the processors in order to perform actions of:
  capturing a voice command and a set of oculesics data corresponding to a user, wherein the voice command is spoken by the user and the set of oculesics data is generated from a smart contact lens worn by the user;
  matching the set of oculesics data to a command augmentation indicator, wherein the command augmentation indicator indicates an augmentation to the voice command;
  aggregating the command augmentation indicator with the voice command into an aggregated command;
  executing the aggregated command by a voice assistance system;
  receiving a different set of oculesics data from the smart contact lens;
  determining that the different set of oculesics data corresponds to a runtime control operation; and
  executing the runtime control operation by the voice assistance system.

10. The information handling system of claim 9 wherein the set of oculesics data is selected from a group consisting of eye lid data, eye tear data, and eye pupil data.

11. The information handling system of claim 10 wherein the processors perform additional actions comprising:
capturing the different set of oculesics data in response to executing the aggregated command;
determining an emotional state of the user based on the different set of oculesics data; and
adjusting a future aggregated command based on the determined emotional state.

12. The information handling system of claim 10 wherein the processors perform additional actions comprising:
receiving the set of oculesics data and the voice command at a mobile device utilized by the user;
performing, by the mobile device, the matching of the set of oculesics data to the command augmentation indicator and the aggregating of the command augmentation indicator with the voice command; and
transmitting the aggregated command from the mobile device to the voice assistance system.

13. The information handling system of claim 9 wherein the processors perform additional actions comprising:
inhibiting the executing of the aggregated command in response to determining that the command augmentation indicator indicates not to execute the voice command.

14. A computer program product stored in a computer readable storage medium, comprising computer program code that, when executed by an information handling system, causes the information handling system to perform actions comprising:
  capturing a voice command and a set of oculesics data corresponding to a user, wherein the voice command is spoken by the user and the set of oculesics data is generated from a smart contact lens worn by the user;
  matching the set of oculesics data to a command augmentation indicator, wherein the command augmentation indicator indicates an augmentation to the voice command;
  aggregating the command augmentation indicator with the voice command into an aggregated command;
  executing the aggregated command by a voice assistance system;
  receiving a different set of oculesics data from the smart contact lens;
  determining that the different set of oculesics data corresponds to a runtime control operation; and
  executing the runtime control operation by the voice assistance system.

15. The computer program product of claim 14 wherein the set of oculesics data is selected from a group consisting of eye lid data, eye tear data, and eye pupil data.

16. The computer program product of claim 15 wherein the information handling system performs further actions comprising:
capturing the different set of oculesics data in response to executing the aggregated command;
determining an emotional state of the user based on the different set of oculesics data; and
adjusting a future aggregated command based on the determined emotional state.

17. The computer program product of claim 15 wherein the information handling system performs further actions comprising:
receiving the set of oculesics data and the voice command at a mobile device utilized by the user;
performing, by the mobile device, the matching of the set of oculesics data to the command augmentation indicator and the aggregating of the command augmentation indicator with the voice command; and
transmitting the aggregated command from the mobile device to the voice assistance system.

\* \* \* \* \*